United States Patent [19]

Ishino et al.

[11] Patent Number: 5,243,081

[45] Date of Patent: Sep. 7, 1993

[54] ALDOL CONDENSATION DEHYDRATION CATALYST, A PROCESS FOR PREPARING THE SAME AND A PROCESS FOR PREPARING AN ALDOL CONDENSATION DEHYDRATE USING THE PROCESS

[75] Inventors: Masaru Ishino, Chiba; Masami Fukao, Shiga; Kazuaki Sasaki, Osaka; Gohfu Suzukamo, Osaka; Masao Sasaki, Osaka, all of Japan

[73] Assignee: Sumitomo Chemical Company, Limited, Osaka, Japan

[21] Appl. No.: 883,397

[22] Filed: May 15, 1992

[30] Foreign Application Priority Data

May 16, 1991 [JP] Japan .................. 3-111520

[51] Int. Cl.$^5$ .............................. C07C 45/74
[52] U.S. Cl. ................... 568/463; 568/345; 568/353; 568/464
[58] Field of Search ............... 568/377, 388, 345, 353, 568/376, 463, 464, 343

[56] References Cited

U.S. PATENT DOCUMENTS

| | | | |
|---|---|---|---|
| 3,791,992 | 2/1974 | Feldwick | 568/377 |
| 4,086,188 | 4/1978 | Reichle | 568/377 |
| 4,165,339 | 8/1979 | Reichle | 568/377 |
| 4,458,026 | 7/1984 | Reichle | 502/80 |
| 4,476,324 | 10/1984 | Reichle | 568/388 |

FOREIGN PATENT DOCUMENTS

| | | |
|---|---|---|
| 146927 | 7/1985 | European Pat. Off. ......... 502/80 |
| 0285386 | 10/1988 | European Pat. Off. . |
| WO8706158 | 10/1987 | PCT Int'l Appl. . |
| WO9012645 | 11/1990 | PCT Int'l Appl. . |
| WO9113831 | 9/1991 | PCT Int'l Appl. . |

OTHER PUBLICATIONS

Tanabe et al. "Addition of Metal Cations to Magnesium Oxide Catalyst for the Aldol Condensation of Actone" Applied Catalysis, 48 (1989) 63-70.

*Primary Examiner*—Werren B. Lone
*Attorney, Agent, or Firm*—Cushman, Darby & Cushman

[57] ABSTRACT

The present invention provides an aldol condensation dehydration catalyst, a process for preparing the same comprising reacting an aluminium salt with at least one magnesium compound selected from the group consisting of magnesium oxide and magnesium hydroxide to support thereon an aluminium compound and heating said supported product at a temperature in the range from 350° to 700° C., and a process for preparing an aldol condensation dehydrate by using the process.

11 Claims, No Drawings

ALDOL CONDENSATION DEHYDRATION CATALYST, A PROCESS FOR PREPARING THE SAME AND A PROCESS FOR PREPARING AN ALDOL CONDENSATION DEHYDRATE USING THE PROCESS

The present invention relates to an aldol condensation dehydration catalyst, a process for preparing the same and a process for preparing an aldol condensation dehydrate by using the process.

As a catalyst for preparing aldol condensation dehydrates by condensing and dehydrating carbonyl compounds such as ketones, aldehydes or the like, that is a catalyst for dehydration by aldol condensation, there are known, for example, (1) a catalyst of supported type in which a calcium salt is supported on alumina and calcined at a temperature from 300° to 600° C. (U.S. Pat. No. 4,535,187) and (2) a catalyst of coprecipitated type in which a coprecipitation product obtained by reacting a solution of a magnesium salt and an aluminium salt with an alkali is calcined at a temperature from 300° to 600° C. (U.S. Pat. Nos. 4,086,188 and 4,476,324).

However, the supported type catalyst (1) had defects such as the complicated preparation method due to the necessity of repreated operations of impregnation and drying until the catalyst reaches the desired concentration of calcium. The coprecipitated type catalyst (2) also had a defect that the coprecipitation product was hard to filter. Thus, neither of the catalysts were satisfactory as industrial catalysts.

Furthermore, it is also known that a catalyst of supported type in which a metal salt is carried on magnesium oxide and calcined at 600° C. produces successfully diacetone alcohol by the aldol condensation of acetone, but that the catalyst activity on supporting an aluminium salt is extensively lowered as compared to magnesium alone [Applied Catalysis, 48, 63 (1989)].

The present inventors have conducted earnest researches in order to find a more preferred aldol condensation dehydration catalyst. As a result thereof, they have found that a catalyst of supported type in which an aluminium compound is supported on a magnesium compound such as magnesium oxide, magnesium hydroxide or the like surprisingly exhibits a high activity as an aldol condensation dehydration catalyst. They have further continued various researches and finally accomplished the present invention.

That is, the present invention provides an aldol condensation dehydration catalyst comprising reacting an aluminium salt with a magnesium compound to support thereon an aluminium compound and heating the supported product at a temperature from 350° to 700° C., a preferred process for preparing industrially an aldol condensation dehydration catalyst comprising reacting an aluminium salt with a magnesium compound to support thereon an aluminium compound and heating the supported product at a temperature from 350° to 700° C., and a preferred process for preparing industrially an aldol condensation dehydrate by condensing a carbonyl compound, characterized in that a catalyst obtained by reacting an aluminium salt with a magnesium compound to support thereon an aluminium compound and heating the supported product at a temperature from 350° to 700° C. is used as a catalyst.

The present invention is now described in more detail.

As the magnesium compound used in the present invention, there are mentioned, for example, magnesium oxide, magnesium hydroxide and the like. Among these magnesium compounds, powders or pellets not less than 200 mesh (Taylor), preferably not less than 500 mesh are usually used. Although magnesium oxide may be either of light or heavy ones, the light one having a larger surface area is preferable.

As the salts of aluminium, there are mentioned, for example, inorganic salts of aluminium such as aluminium nitrate, hydrochloride, sulfate and perchlorate, sodium aluminate, sodium aluminium sulfate and ammonium aluminium sulfate, and organic salts of aluminium such as aluminium lactate and the like. Among these salts, aluminium nitrate and lactate are preferred.

The ratio of the amount of the aluminium salt used to the amount of magnesium compound is generally in a proportion of ½ to 1/100, preferably from ⅓ to 1/50 by atomic ratio.

While the reaction of the aluminium salt with the magnesium compound to support thereon the aluminium compound can be carried out by adding the magnesium compound to an aluminium solution in a solvent, the addition of the aluminium solution in a solvent to the suspension of the magnesium compound in a solvent is preferred. As the solvent, there are mentioned, for example, water, a lower alcohol, a lower ketone and the like, among which water is generally used.

While the supported product is obtained by removing a solvent, it can be also obtained by separating the solvent by an appropriate means such as filtration or the like. The supported product can be further subjected to washing.

Calcination of the supported product is carried out at a temperature from about 350° to 700° C. Heating of the supported product at a temperature below about 350° C. or exceeding about 700° C. is not preferred because the catalyst activity is lowered.

The period of calcination by heating, which depends on the heating temperatures, is usually in a period from 0.1 to about 10 hours.

The catalyst according to the present invention is thus obtained, and the ratio of aluminium to magnesium is usually in a proportion of ½ to 1/50 by atomic ratio.

The catalyst of the present invention is excellent as a dehydration catalyst by aldol condensation.

When the catalyst is used as an aldol condensation dehydration catalyst, it may be supported on a carrier, or it may be diluted with a diluent such as glass beads or the like. It is also possible to improve the properties such as mechanical strength or the like by adding to it a binder such as alumina sol or the like.

The reaction can be conducted by any means of batchwisely or continuously. When the reaction is conducted continuously, any catalysts in the type of a fixed bed or a fluidized bed can be employed. Moreover, the catalyst of which the activity has been lowered can also be regenerated by calcination in the presence of air.

As the raw materials of the dehydration by aldol condensation, there are mentioned carbonyl compounds, for example, ketones such as acetone, methyl ethyl ketone, methyl isobutyl ketone and the like, and aldehydes such as acetaldehyde, butylaldehyde and the like.

Condensation and dehydration reaction can be conducted in accordance with the well known methods.

For example, when mesytyl oxide and isophorone are prepared with acetone, the reaction is conducted generally at a temperature from 250° to 400° C., preferably from 270° to 330° C., at a pressure from atmospheric pressure to 10 kg/cm². The raw material is supplied generally at a rate such as LHSV (liquid hourly space velocity) from 0.1 to 10 h$^{-1}$, preferably from 1 to 5 h$^{-1}$.

The catalyst of supported type according to the present invention has excellent properties as a dehydration catalyst by aldol condensation and gives efficiently dehydration products by condensation.

The present invention is described in detail with reference to examples without limit thereto.

EXAMPLE 1

To 1142 g of deionized water in a 3-liter flask was suspended 103.8 g of magnesium oxide (surface area; about 150 m²/g) under the nitrogen atmosphere at a temperature from 25° to 30° C., and a solution of 193.3 g of deionized water and 96.7 g of aluminium nitrate nonahydrate was added dropwise to the suspension over a period of about 0.5 hour.

The resulting mixture was stirred at the same temperature for about 3 hours, filtered and washed with 1142 g of deionized water, and the residue was dried at 130° C.

The residue was next subjected to calcination at 550° C. for 3 hours to give 81 g of a white solid.

EXAMPLE 2

To 300 g of deionized water in a 1-liter flask was suspended 100 g of the same magnesium oxide as used in Example 1 under the nitrogen atmosphere at a temperature from 25° to 30° C., and a solution of 100 g of deionized water and 93.1 g of aluminium nitrate nonahydrate was added dropwise to the suspension over a period of about 0.5 hour.

Then, 500 g of deionized water was added to the mixture and the resulting mixture was stirred at the same temperature for about 3 hours, concentrated under a temperature from 80° to 100° C./30 mmHg and calcined at 550° C. for 3 hours to give 80.6 g of a white solid.

EXAMPLE 3

To 450 g of deionized water in a 1-liter flask was suspended 40.3 g of the same magnesium oxide as used in Example 1 under the nitrogen atmosphere at a temperature from 25° to 30° C., and a solution of 32.15 g of deionized water and 17.86 g of aluminium nitrate nonahydrate was added dropwise to the suspension over a period of about 0.5 hour.

Then, after stirring at the same temperature for about 3 hours, the mixture was filtered, washed with 450 g of deionized water and dried at a temperature of 130° C.

The dried product was then calcined at 550° C. for 3 hours to give 37.29 g of a white solid.

EXAMPLE 4

The procedure in Example 3 was repeated except that a solution of 42.86 g of deionized water and 7.14 g of aluminium nitrate nonahydrate was added dropwise to the suspension to give 35.96 g of a white solid.

EXAMPLE 5

The procedure in Example 3 was repeated except that a solution of 142.84 g of deionized water and 107.16 g of aluminium nitrate nonahydrate was added dropwise to the suspension to give 38.65 g of a white solid.

EXAMPLE 6

The procedure in Example 3 was repeated except that 58.32 g of magnesium hydroxide was employed in place of magnesium oxide and a solution of 64.29 g of deionized water and 35.71 g of aluminium nitrate nonahydrate was added dropwise to the suspension to give 35.84 g of a white solid.

EXAMPLE 7

To 20 g of deionized water in a flask having a volume of 300 ml was suspended 25 g of magnesium oxide under the nitrogen atmosphere at a temperature from 25° to 30° C., and a solution of 100 g of deionized water and 9.16 g of aluminium lactate was added dropwise to the suspension.

Then, after stirring at the same temperature for about 3 hours, the mixture was concentrated under a temperature from 80° to 100° C./30 mmHg and calcined at 500° C. for 2 hours to give 20.82 g of a white solid.

EXAMPLE 8

To a solution of 400 g of deionized water and 153.8 g of magnesium nitrate hexahydrate was added dropwise a solution of 150.2 g of a 28% aqueous ammonia solution and 200 g of deionized water over a period of about 0.5 hour followed by a solution of 75 g of aluminium nitrate nonahydrate and 200 g of deionized water over a period of about 0.5 hour, and the mixture was stirred at the same temperature for about 3 hours.

Then, the mixture was filtered, washed with deionized water, dried at 200° C. and calcined at 500° C. for 3 hours to give 34.4 g of a white solid.

COMPARATIVE EXAMPLE 1

A white solid was obtained by calcining 100 g of the same magnesium oxide as used in Example 1 at 550° C. for 3 hours.

EXAMPLES 9-17, COMPARATIVE EXAMPLE 2

In a reaction tube of stainless steel (internal diameter 16 mm$\phi$×250 mm) was filled 10 ml of a catalyst prepared in Examples 1-8 or Comparative Example 1 (formed into a particle size of 24-48 mesh), and nitrogen gas was supplied at a rate of 20 ml/min to maintain an internal pressure at 2.8 kg/cm²G. Subsequently, after the temperature of the reaction tube was raised to 300° C., acetone was supplied at a rate of 10 ml/hour. After the reaction for about 18 hours, the reaction mixture eluted was sampled and analyzed by gas chromatography to determine the content of the products. Then, the content of the products were determined while the flow rate of acetone was varied within the range from 5 to 60 ml/hour. The results are shown in Table 1.

In this connection, the recovery of the reaction mixture was in the range from 98 to 99% based on the amount of acetone used.

TABLE 1

| Example | Catalyst | Flow rate of acetone | Composition of reaction mixture (% by weight) | | |
|---|---|---|---|---|---|
| | | | Acetone | Mesityl oxide | Isophorone |
| Example 9 | Example 1 | 10 ml/h | 67.2 | 3 | 15.7 |
| | | 30 | 70 | 2.7 | 15.4 |
| | | 40 | 75.5 | 3.1 | 12.0 |
| Example 10 | Example 2 | 10 | 64.8 | 2.9 | 17.4 |
| | | 30 | 76.5 | 3.7 | 11.4 |
| | | 40 | 78.7 | 3.7 | 10.1 |

TABLE 1-continued

| Example | Catalyst | Flow rate of acetone | Composition of reaction mixture (% by weight) | | |
|---|---|---|---|---|---|
| | | | Acetone | Mesityl oxide | Isophorone |
| Example 11 | Example 3 | 9 | 71.2 | 3.6 | 12.5 |
| | | 28 | 84.2 | 3.6 | 7.7 |
| | | 51.5 | 86.4 | 3.4 | 6.7 |
| Example 12 | Example 4 | 9.2 | 77.5 | 4.3 | 9.8 |
| | | 28.9 | 87.2 | 3.8 | 5.7 |
| | | 50.6 | 89.6 | 4.4 | 4.5 |
| Example 13 | Example 5 | 9.3 | 60.1 | 2.6 | 17 |
| | | 29.2 | 70.9 | 3.6 | 14.1 |
| | | 51.1 | 75.8 | 3.7 | 12.1 |
| Example 14 | Example 6 | 8.3 | 67.3 | 3.8 | 13.8 |
| | | 29 | 79.4 | 4.6 | 9.2 |
| | | 52.3 | 84.8 | 4.4 | .6 |
| Example 15 | Example 7 | 10.1 | 76.2 | 5.5 | .1 |
| | | 19.6 | 82 | 5.6 | 4.7 |
| | | 29.5 | 84.5 | 5.5 | 3.9 |
| Example 16 | Example 8 | 8.9 | 60.6 | 2.4 | 18.5 |
| | | 19.4 | 67.3 | 3.2 | 15.2 |
| | | 39 | 77.4 | 3.5 | 10.8 |
| Comparative Example 2 | Comparative Example 1 | 5 | 76.6 | 10.5 | 2.9 |
| | | 11.4 | 78.2 | 11.2 | 2.2 |
| | | 24.5 | 84.9 | 9.9 | 0.6 |

Mesityl oxide: 4-methyl-3-penten-2-one + 4-methyl-4-penten-2-one.
Isophorone: 3,5,5-trimethyl-2-cyclohexen-1-one + 3,5,5-trimethyl-3-cyclohexen 1-one

EXAMPLE 17

Example 8 was repeated except that cycloxanone was used in place of the acetone. After about 10 hours, a reaction solution was assayed by gas chromatography. The results were

| | |
|---|---|
| 2-cyclohexylidene-cyclohexanone | 3.4% by weight |
| 2-(1-cyclohexenyl)cyclohexanone | 0.6% by weight |
| cyclohexanone | 93.8% by weight |

What is claimed is:

1. A process for preparing an aldol condensation dehydration product comprising:
condensing and dehydrating at least one compound selected from the group consisting of lower alkyl ketones and aldehydes in the presence of a catalytically effective amount of a supported catalyst whereby an aldol condensation product is obtained, said catalyst being obtained by reacting an aluminum salt with at least one magnesium compound selected from the group consisting of magnesium oxide and magnesium hydroxide to support thereon an aluminum compound whereby a catalyst is obtained, and heating the thus obtained catalyst at a temperature ranging from 350° C. to 700° C.

2. A process according to claim 1, wherein said carbonyl compound is acetone cyclohexanone.

3. A process according to claim 1, wherein said magnesium compound has a particle size in the range of 500 mesh or more.

4. A process according to claim 1, wherein said magnesium compound is light magnesium oxide.

5. A process according to claim 1, wherein said aluminium salt is aluminium nitrate, hydrochloride, sulfate or perchlorate, sodium aluminate, sodium aluminium sulfate, ammonium aluminium sulfate, aluminium lactate, aluminium acetate or aluminium propionate.

6. A process according to claim 1, wherein said aluminium salt is aluminium nitrate or sulfate.

7. A process according to claim 1, wherein the ratio of the amount of the aluminium salt used to the amount of magnesium compound is in a proportion of $\frac{1}{2}$ to 1/100 by atomic ratio.

8. A process according to claim 1, wherein the process for supporting an aluminium compound by reacting an aluminium salt with a magnesium compound is a process for adding an aluminium salt solution in a solvent to a magnesium compound dispersion in a solvent.

9. A process according to claim 1, wherein said solvent is water.

10. A process according to claim 1, wherein said carbonyl compound is selected from the group consisting of acetone, methyl ethyl ketone, methyl isobutyl ketone, acetaldehyde, and butylaldehyde.

11. A process according to claim 1, wherein the process for preparing an aldol condensation dehydration product is conducted at a temperature of from 250° C. to 400° C. at a pressure up to 10 kg/cm$^2$.

* * * * *